United States Patent
Bailey et al.

(10) Patent No.: US 9,414,806 B2
(45) Date of Patent: *Aug. 16, 2016

(54) ULTRASOUND BASED METHOD AND APPARATUS TO DETERMINE THE SIZE OF KIDNEY STONE FRAGMENTS BEFORE REMOVAL VIA URETEROSCOPY

(71) Applicants: University of Washington Through Its Center for Commercialization, Seattle, WA (US); University of British Columbia, Vancouver (CA)

(72) Inventors: Michael Bailey, Seattle, WA (US); Joel Teichman, West Vancouver (CA); Mathew Sorensen, Seattle, WA (US)

(73) Assignees: University of Washington, Seattle, WA (US); University of British Columbia, Vancouver (CA)

( * ) Notice: Subject to any disclaimer, the term of this patent is extended or adjusted under 35 U.S.C. 154(b) by 361 days.

This patent is subject to a terminal disclaimer.

(21) Appl. No.: 14/079,874

(22) Filed: Nov. 14, 2013

(65) Prior Publication Data

US 2014/0194737 A1 Jul. 10, 2014

Related U.S. Application Data

(63) Continuation of application No. 12/469,086, filed on May 20, 2009, now Pat. No. 8,607,634, which is a continuation-in-part of application No. 11/872,668, filed on Oct. 15, 2007, now Pat. No. 8,535,250.

(60) Provisional application No. 61/054,640, filed on May 20, 2008.

(51) Int. Cl.
*A61B 8/08* (2006.01)
*A61B 8/12* (2006.01)
(Continued)

(52) U.S. Cl.
CPC .................. *A61B 8/12* (2013.01); *A61B 5/1076* (2013.01); *A61B 8/08* (2013.01); *A61B 8/5215* (2013.01); *A61B 17/2256* (2013.01); *A61B 1/307* (2013.01); *A61B 17/22012* (2013.01)

(58) Field of Classification Search
CPC .......... A61B 8/08; A61B 8/12; A61B 8/5215; A61B 5/1076; A61B 1/307
See application file for complete search history.

(56) References Cited

U.S. PATENT DOCUMENTS 3,606,879 A 9/1971 Estes
4,375,818 A 3/1983 Suwaki et al.
(Continued)

FOREIGN PATENT DOCUMENTS

WO WO 2009/049148 A1 4/2009

OTHER PUBLICATIONS

Bailey et al., "*Cavitation Detection During Shock-Wave Lithotripsy*", Ultrasound in Med. & Biol., vol. 31, No. 9, pp. 1245-1256, Copyright © 2005, 12 pages.

(Continued)

*Primary Examiner* — Joel Lamprecht
(74) *Attorney, Agent, or Firm* — Kilpatrick Townsend and Stockton LLP (57) ABSTRACT

A transducer is used to send an ultrasound pulse toward a stone and to receive ultrasound reflections from the stone. The recorded time between a pulse that is reflected from the proximal surface and a pulse that is reflected either from the distal surface of the stone or from a surface supporting the stone is used to calculate the stone size. The size of the stone is a function of the time between the two pulses and the speed of sound through the stone (or through the surrounding fluid if the second pulse was reflected by the surface supporting the stone). This technique is equally applicable to measure the size of other in vivo objects, including soft tissue masses, cysts, uterine fibroids, tumors, and polyps.

20 Claims, 6 Drawing Sheets

(51) Int. Cl.
  *A61B 5/107*    (2006.01)
  *A61B 17/225*   (2006.01)
  *A61B 1/307*    (2006.01)
  *A61B 17/22*    (2006.01)

(56) References Cited

U.S. PATENT DOCUMENTS

| | | | |
|---|---|---|---|
| 4,665,751 | A | 5/1987 | Huschelrath |
| 4,899,733 | A | 2/1990 | DeCastro et al. |
| 4,942,878 | A | 7/1990 | Dory |
| 4,976,255 | A | 12/1990 | Reichenberger et al. |
| 5,209,234 | A | 5/1993 | LaRocca |
| 6,567,688 | B1 | 5/2003 | Wang |
| 6,902,528 | B1 | 6/2005 | Garibaldi et al. |
| 8,535,250 | B2 | 9/2013 | Owen et al. |
| 8,607,634 | B2 * | 12/2013 | Bailey .................. A61B 5/1076 600/437 |
| 2003/0040737 | A1 | 2/2003 | Merril et al. |
| 2005/0033314 | A1 | 2/2005 | Sakurai et al. |
| 2007/0123518 | A1 | 5/2007 | Epshtein |
| 2014/0081174 | A1 | 3/2014 | Owen et al. |

OTHER PUBLICATIONS

Bohris et al., "*Hit/Miss Monitoring of ESWL by Spectral Doppler Ultrasound*", Ultrasound in Med. & Boil., vol. 29, No. 5, pp. 705-712, Copyright © 2006, 8 pages.

Chang et al., "*In Vitro Study of Ultrasound Based Real-Time Tracking of Renal Stones for Chock Wavy Lithotripsy: Part 1*", The Journal of Urology, vol. 166, pp. 28-32, Jul. 2001, 5 pages.

Choung et al., "*Acoustic and Mechanical Properties of Renal Calculi: Implications in Shock Wave Lithotripsy*", Journal of Endourology, vol. 7, No. 6, 1993, pp. 437-444, 8 pages.

Cleveland et al., "*Modeling Elastic Wave Propagation in Kidney Stones With Application to Shock Wave Lithotripsy*", J. Acoust. Soc. Am. 118 (4), pp. 2667-2676, 10 pages.

Fedele et al., "*Development of a New Diagnostic Sensor for Extra-Corporeal Shock-Wave Lithotripsy*", Journal of Physics: Conferences Serices 1 (2004), pp. 134-139, 6 pages.

Goldberg et al., "*Endoluminal Sonography of the Urinary Tract: Preliminary observations*", Am J Roentgenology 1991, vol. 156, pp. 99-103, 5 pages.

McAteer et al., "*Strategies for Improved Shock Wave Lithotripsy*", Minerva Urologica E Nefrologica, vol. 57, No. 4, pp. 271-287, Dec. 2005, 17 pages.

Orkisz et al., "*Real-Time Target Tracking Applied to Improve Fragmentation of Renal Stones in Extra-Corporeal Lithotripsy*", Machine Vision and Applications, 1999, 11:138-144, 7 pages.

Owen et al., "*Characterization of a Vibro-Acoustography System Designed to Detect Kidney Stones During Lithotripsy*", J. Acoust. Soc. Am., vol. 117, No. 4, Part 2, p. 2588, Apr. 2005, 22 pages.

Owen et al., "*Vibro-Acoustography for Targeting Kidney Stones During Lithotripsy*", J. Acoust. Soc. Am., vol. 116, No. 4, Part 2, p. 2509, Oct. 2004, 16 pages.

Sapozhnikov et al., "*Detecting Fragmentation of Kidney Stones in Lithotripsy by Means of Shock Wave Scattering*", 5th International Symposium on Therapeutic Ultrasound, Oct. 27-29, 2005, Published online on May 2006, http://proceedings.aip.org/resource/2/apcpcs/829/1?isAuthorized=no, 5 pages.

Sapozhnikov et al., "*Modeling of Stresses Generated by Lithotripter Shock Wave in Sylindrical Kidney Stone*", Proc. Of ISTU3, ed. By Chapelon et al., INSERM, Lyon, 2003, pp. 323-328, 6 pages.

Schafer et al., "*Design of a Miniature In-Vivo Shock Wave Hydrophone*", Ultrasonics Symposium, 1990. Proceedings., IEEE 1990, vol., No., pp. 1623-1626 vol. 3, Dec. 1990. doi: 10.11 09/ULTSYM.1990.171643, 4 pages.

Non-Final Office Action for U.S. Appl. No. 11/872,668 mailed on Jul. 15, 2011, 14 pages.

Non-Final Office Action for U.S. Appl. No. 12/469,086 mailed on Aug. 9, 2011, 14 pages.

Final Office Action for U.S. Appl. No. 12/469,086 mailed on May 24, 2012, 14 pages.

Non-Final Office Action for U.S. Appl. No. 11/872,668 mailed on May 25, 2012, 13 pages.

Non-Final Office Action for U.S. Appl. No. 11/872,668 mailed on Dec. 26, 2012, 19 pages.

Notice of Allowance for U.S. Appl. No. 11/872,668 mailed on May 14, 2013, 5 pages.

Notice of Allowance for U.S. Appl. No. 12/469,086 mailed on Aug. 14, 2013, 5 pages.

\* cited by examiner

ULTRASOUND BASED METHOD AND APPARATUS TO DETERMINE THE SIZE OF KIDNEY STONE FRAGMENTS BEFORE REMOVAL VIA URETEROSCOPY

CROSS-REFERENCES TO RELATED APPLICATIONS

The present application is a Continuation of U.S. Ser. No. 12/469,086 filed May 20, 2009 (Allowed), which application claims the benefit of U.S. Provisional Appln. No. 61/054,640 filed May 20, 2008 and is also a continuation-in-part of U.S. Ser. No. 11/872,668 filed Oct. 15, 2007 (now U.S. Pat. No. 8,535,250). The full disclosures, each of which are incorporated herein by reference in their entirety, for all purposes.

GOVERNMENT RIGHTS

This invention was made with government support under grant number DK43881 awarded by National Institutes of Health (NIH) and grant number SMS00402 awarded by National Space Biomedical Research Institute (NSBRI). The government has certain rights in the invention.

BACKGROUND OF THE INVENTION

Ureteroscopy often requires extraction of stone fragments by grasping them in a basket and pulling them out of the body along the ureteral tract. Urologists occasionally attempt to remove such stone fragments only to find that the fragment is too large to remove through the ureter, since endoscopic stone fragment size estimates are subjective and can be in error. Currently, no intra-operative tools are available to measure fragment size before such removal is attempted. Clearly, it would be desirable to develop an approach to more accurately determine stone fragment size before an attempt is made to extract them.

BRIEF SUMMARY OF THE INVENTION

This application specifically incorporates by reference the disclosures and drawings of each patent application identified above as a related application.

The concepts disclosed herein employ ultrasound to enable an inter-operative tool to be used for estimating a size of an in vivo object. In an exemplary, but non-limiting embodiment and application of this novel approach, the object is a kidney stone fragment, and the inter-operative tool is a ureteroscope. In general, two echoes are detected, a first echo corresponding to a proximal surface of the object, and a second echo corresponding to a distal surface of the object (or a distal surface supporting the object). The speed of sound in the object (or the ambient fluid surrounding the distal surface supporting the object) is then used to calculate a distance between the proximal and distal surfaces of the object.

In a first variation of this technique, the source transducer is aligned such that the ultrasound pulse travels through the object, from the proximal surface to the distal surface. If the object is disposed in a fluid that effectively couples the ultrasound from the transducer to the object (such as an aqueous liquid), the transducer can be spaced apart from the object.

In a second exemplary variation of this technique, the source transducer is aligned such that a portion of the ultrasound pulse is reflected by a proximal surface of the object, and a portion of the ultrasound pulse is reflected by a distal surface supporting the object. The second variation is particularly effective when an acoustic path between the distal surface supporting the object and the ultrasound transducer is uninterrupted.

While the concepts disclosed herein can be beneficially employed to determine the size of kidney stone fragments during a ureteroscopic procedure, it should be recognized that these concepts can also be used to estimate the size of other objects during an inter-operative procedure, including but not limited to, the size of stones in the pancreatic tract, the size of stones in the gall bladder, the size of stones in bile ducts, the size of stones in salivary ducts, and the size of in vivo tissue objects (including but not limited to cysts, fibroids, tumors, and polyps).

The transducer employed can be incorporated into a distal end of an inter-operative instrument (such as a ureteroscope), or can be incorporated into a distal end of elongate flexible body delivered through a working lumen of an inter-operative instrument. It should be understood that, depending on the in vivo location and the procedure being implemented, the ultrasound transducer can be incorporated into the distal end of a probe that does not need to be sized to fit through a lumen of another instrument.

It should be noted that while the use of ultrasound (i.e., sound above the range of human hearing, generally accepted to be sound having a frequency of greater than about 20,000 Hz) represents an exemplary embodiment, it should be recognized that similar results theoretically could be obtained using different frequencies not normally associated with the term ultrasound. In general, higher frequencies are preferred, as lower frequencies are less directive, pulses at lower frequencies are longer, so more processing is required to identify a small time difference between two long signals, and long low frequency signals don't scatter well off of small objects (leading to weaker signals).

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

BRIEF DESCRIPTION OF THE DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

DETAILED DESCRIPTION OF THE INVENTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

As noted above, the concepts disclosed herein employ ultrasound to enable a medical tool to estimate a size of an in vivo object. In an exemplary, but non-limiting embodiment, the object is a kidney stone or fragment thereof, and the inter-operative tool is a ureteroscope. Kidney stones or stone fragments are often removed through narrow tubes during ureteroscopy. Thus, one aspect of the concepts described herein is a device to measure stone size before attempting to remove a stone or stone fragment that is too large to fit through an available lumen. Attempting to extract a stone that is too large wastes time and increases the chance of injuring biological passages, such as the ureter. In general, the technique disclosed herein employs an ultrasound element that is sufficiently small to be incorporated into a distal end of a ureterscope, or sufficiently small to be advanced through a working lumen of a ureterscope, to send ultrasound and also receive ultrasound reflections from the object, whose size is to be measured (for ureteroscopy, the object will normally be a stone or stone fragment). The time between reflections collected from the proximal and the distal surfaces of the object, along with the speed of sound, are used to calculate the object size. The speed of sound can be that in the stone or in the surrounding fluid, depending on how the medical practitioner orients the ultrasound instrument.

It should be noted that while the present novel approach of measuring the size of kidney stones (or fragments thereof) during ureteroscopy represents an exemplary embodiment, the concepts disclosed herein can also be used to measure the size of other types of in vivo objects, including, but not limited to, mineral deposits and stones in the gall bladder, in the salivary tract, and in the biliary tract. Furthermore, the same novel concepts can be used to measure tissue-based in vivo objects, including, but not limited to, cysts, polyps, uterine fibroids, tumors, and other tissue masses, as well as foreign objects (such as objects that have been swallowed or otherwise ingested, and objects that have been intentionally or unintentionally introduced into a patient's body during a medical procedure). Ultrasound transducers for sizing purposes can be incorporated into many different types of medical instruments, in addition to ureteroscopes, such as catheters, surgical tools, biopsy, endoscopic and laparoscopic tools, and medical probes. As discussed in greater detail below, the design of existing medical tools can be modified to include an ultrasound transducer, or a separate tool having the transducer disposed at its distal end can be fabricated for use during a medical procedure.

Figure 1A:
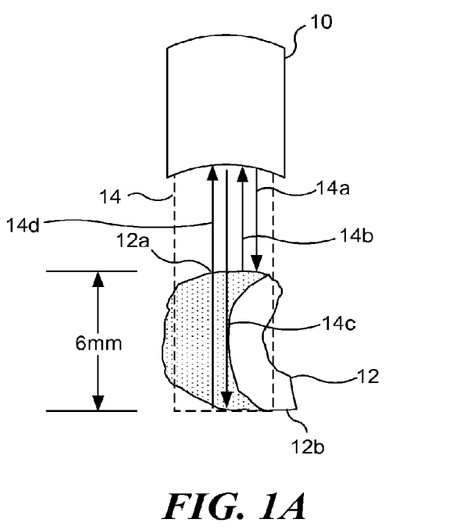
FIG. 1A schematically illustrates a first exemplary embodiment employing the concepts disclosed herein, wherein ultrasound is used to determine a size of an in vivo object during an operative procedure, and wherein the size is calculated based on a speed of sound in the object, and a time interval between a first echo collected from a proximal surface of the object, and a second echo collected from a distal surface of the object.

FIG. 1A schematically illustrates a first exemplary embodiment embodying the novel concepts disclosed herein, wherein ultrasound is used to determine a size of an in vivo object during an operative procedure. The size of the object is calculated based on a speed of sound in the object, and a time interval between a first echo collected from a proximal surface of the object, and a second echo collected from a distal surface of the object.

Referring to FIG. 1A, an ultrasound transducer 10 is disposed adjacent to an object 12 (such as a kidney stone) so that ultrasound energy propagates generally along a path 14. So long as the ambient environment conducts ultrasound waves, the transducer need not be in contact with the object. Bodily fluids such as water, blood, and urine will conduct ultrasound waves with less loss than tissue. When the ultrasound transducer is energized, a portion 14a of the ultrasound pulse encounters a proximal surface 12a of the object, causing an echo or reflection 14b to return to the transducer for collection. Similarly, a portion 14c of the ultrasound pulse passes through the object and encounters a distal surface 12b of the object, causing an echo or reflection 14d to return to the transducer for collection. In an empirical study discussed in detail below, this technique was successfully used to measure stones that were approximately 6 mm in length, but this size should not be construed as a limitation.

Thus, in this first exemplary illustration, the source transducer is aligned such that the ultrasound pulse travels through the object, from the proximal surface to the distal surface. The distance between the proximal and distal surfaces is calculated using the following relationship:

$$D = c_1 t/2 \tag{1}$$

where t is the time between the two reflected pulses, D is the distance between the proximal and distal surfaces, and $c_1$ is the speed of sound in the object.

Note that dividing by 2 in Eq. (1) is required because the pulse passes through the object once, is reflected from the distal surface, and passes back through the object a second time. Where the object is a kidney stone, $c_1$ can be assumed to be 4300 m/s (although as will be discussed in detail below, useful measurements were also obtained using 3000 m/s for $c_1$). The speed of sound in different types of stones does vary, and if the specific type of stone is known, the speed of sound for that type of stone can be used. However, the empirical studies discussed below indicate that useful sizing results can be obtained using an estimated value for $c_1$. Where the object is a tissue mass (such as a cyst, a tumor, or a polyp), $c_1$ can be assumed to be 1540 m/s. The speed of sound in different types of tissue also varies, and if the speed of sound for a specific tissue type is known, that value can be employed for improved accuracy.

Figure 1B:
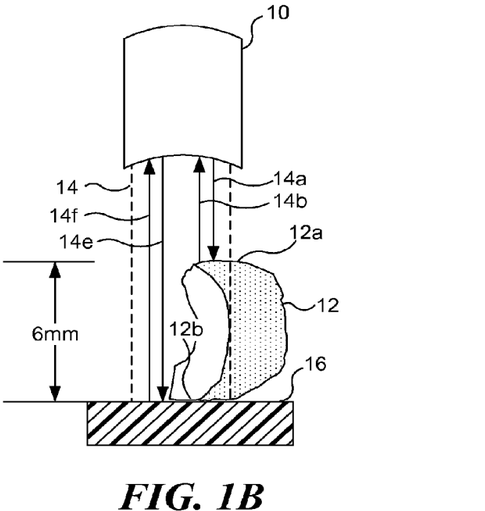
FIG. 1B schematically illustrates a second exemplary embodiment employing the concepts disclosed herein, wherein ultrasound is used to determine a size of an in vivo object during an operative procedure, and wherein the size is calculated based on a speed of sound in ambient fluid surrounding the object, and a time interval between a first echo collected from a proximal surface of the object, and a second echo collected from a distal surface supporting the object.

FIG. 1B schematically illustrates a second exemplary embodiment embodying the concepts disclosed herein, wherein ultrasound is used to determine a size of an in vivo object during an operative procedure. However, in this embodiment, the object size is calculated based on a speed of sound in ambient fluid surrounding the object, and a time interval between a first echo collected from a proximal surface of the object, and a second echo collected from a distal surface supporting the object.

Referring to FIG. 1B, ultrasound transducer 10 is disposed adjacent to an object 12 (such as a kidney stone), but offset such that ultrasound pulses reflect from both a proximal surface of the object and a distal surface supporting the object. As with the exemplary embodiment of FIG. 1A, when the ultrasound transducer is energized, a portion 14a of the ultrasound pulse encounters a proximal surface 12a of the object, causing an echo or reflection 14b to return to the transducer for collection. However, because of the orientation of the transducer, a portion 14e of the ultrasound pulse passes through the ambient fluid alongside the object and encounters a distal surface 16 that supports the object, causing an echo or reflection 14f to return to the transducer for collection.

Thus, in this second exemplary embodiment employing the novel sizing technique, the source transducer is aligned such that a portion of the ultrasound pulse is reflected by a proximal surface of the object and a portion of the ultrasound pulse is also reflected by a distal surface supporting a distal surface of the object. The distance between the proximal and distal surfaces of the object can then be calculated using the following relationship:

$$|D = c_2 t/2| \quad (2)$$

where t is the time between the two reflected pulses, D is the distance between the proximal and distal surfaces, and $c_2$ is the speed of sound in the ambient fluid surrounding the object.

Again, dividing by 2 in Eq. (2) is required because the transmitted pulse passes alongside the object once, is reflected from the distal surface supporting the object, and passes back alongside the object a second time. Where the object is a kidney stone, $c_2$ can be assumed to be 1481 m/s (the speed of sound in water—urine in practice) at 20 degrees Celsius. Empirical studies indicate that useful sizing results can be obtained using this value for $c_2$. Where the object is disposed in a different fluid environment, the speed of sound for that fluid can be used for $c_2$ (so long as the fluid is capable of propagating an ultrasound pulse). Note that this second variation is particularly effective when an acoustic path between the distal surface supporting the object and the ultrasound transducer is uninterrupted. In an in vivo environment where an acoustical path from the transducer to a distal surface supporting the object is obstructed, the first exemplary embodiment is likely to be more readily implemented. It will be appreciated that if the speed of sound for the ambient fluid can be determined or estimated with greater accuracy than the speed of sound in the object, then the measurements from the second exemplary embodiment are likely to be more accurate (assuming that either embodiment can be used without any difficulty).

With respect to the exemplary embodiment of FIG. 1B, it should be noted that the parameters noted above are based on the object resting on a distal surface (such as tissue) and being surround by a fluid (such as blood or urine). In cases where the object is surrounded by tissue, the exemplary embodiment of FIG. 1A will likely be more useful, unless the tissue surrounding the object is different than the tissue supporting the object. If the tissue surrounding the object is contiguous with the tissue supporting the object, then there will be no interface at the distal surface to reflect the acoustic pulse when implementing the exemplary embodiment of FIG. 1B.

Figure 2A:
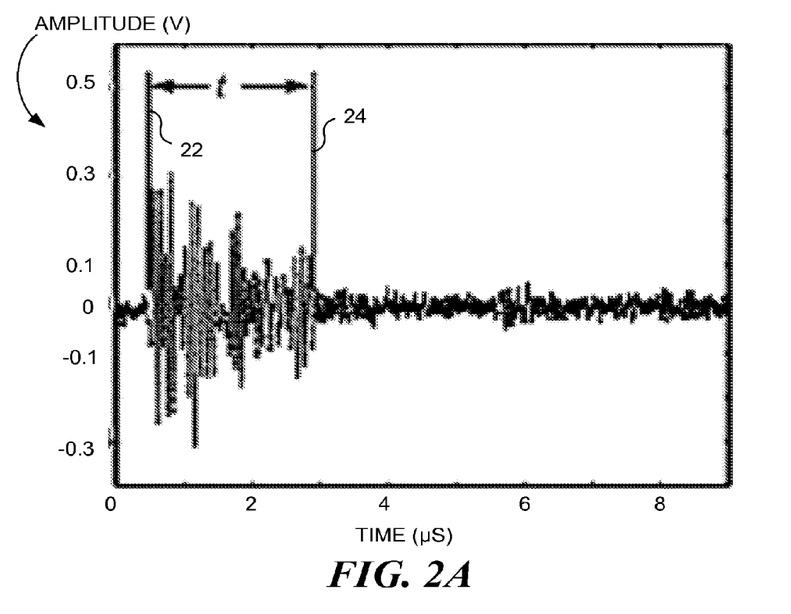
FIG. 2A graphically illustrates empirical data collected using the embodiment of FIG. 1A.

FIG. 2A graphically illustrates empirical data collected using the exemplary embodiment of FIG. 1A for a particular stone. From the signal, a first peak 22 is identified as being indicative of the first reflection at the proximal surface of the object, and a second peak 24 is identified as being indicative of the second reflection at the distal surface of the object.

It should be noted that identifying the peaks must take into consideration the following factors. The overall signal includes a reflection from the proximal and distal surfaces of the stone, as well as reflections from any internal structure in the stone. The signal is further complicated by extra reverberation inherent in the stone and the transducer. Finally, the interrogation pulse from the transducer has a certain duration. For example, the empirical data for the ex vivo testing was collected using a relatively short interrogation pulse of ~5 cycles of the transducer source frequency. Consider the analogy of a person trying to generate an echo by yelling; one generally shouts "echo" rather than just "O". Clearly, the duration of the "echo" interrogation pulse is longer than the duration of the "O" interrogation pulse. To continue with that analogy, the time interval that is required is the time interval between a first "echo" (from the proximal surface) and a second "echo" (from the distal surface) in response to the "echo" interrogation pulse. The time interval between the "e" in the first "echo" (from the proximal surface) and the "o" in the second "echo" (from the distal surface) is referred to as the total duration. Ideally, one would be able to extract from the signal the time (i.e., the location of a peak) for the "e" in the first "echo" (from the proximal surface) and the "e" in the second "echo"; i.e., the starting time for each echo. Because the first and second echoes can overlap in time, identifying those peaks from a signal can require signal processing as opposed to simply visually identifying peaks from a graphical display of the signal. For example, the "e" in the second "echo" (from the distal surface) might actually be received at the same time as the "h" in the first "echo" (from the proximal surface). Because of this issue, the data collected in the ex vivo testing determined the time interval using the total duration, as opposed to specifically identifying the beginning of the first and second echoes. Significantly, even such an approximation provided useful results. A subsequent study (discussed below) employed signal processing techniques to extract the beginning of the first and second echoes from the signal.

Figure 2B:
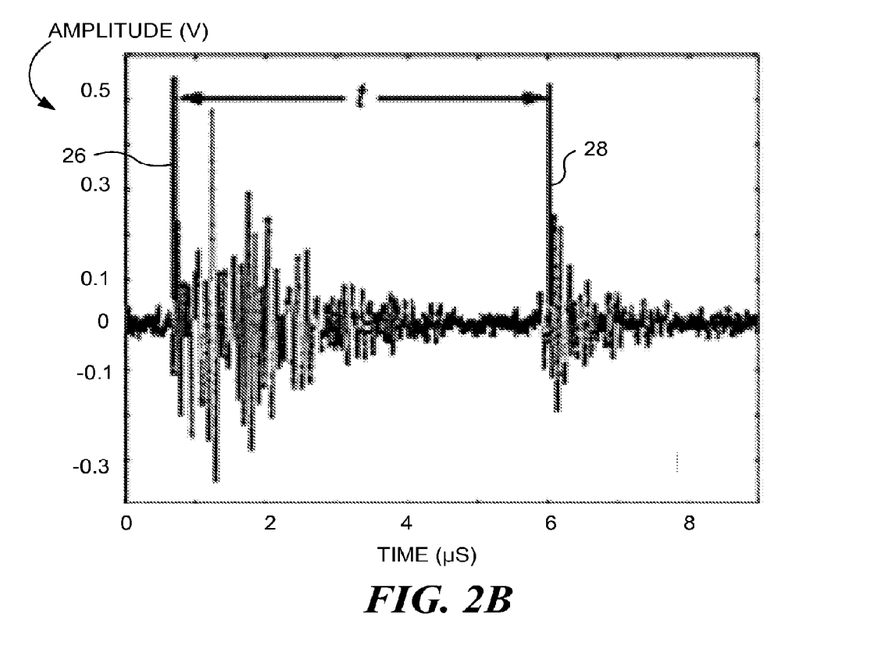
FIG. 2B graphically illustrates empirical data collected using the embodiment of FIG. 1B.

FIG. 2B graphically illustrates empirical data collected using the embodiment of FIG. 1B (from the same stone for which data collected using the embodiment of FIG. 1A is graphically displayed in FIG. 2A). Again, a first peak 26 is indicative of the first reflection at the proximal surface of the object, and a second peak 28 is indicative of the second reflection at the distal surface supporting the object. As discussed above, in the first ex vivo study the total duration was employed, as opposed to using signal processing techniques to determine more precise locations for the beginning of the first and second echoes, thus such peaks in FIGS. 2A and 2B are simply intended to generally indicate the locations of the beginning of the first and second echoes. Note that t measured with the embodiment of FIG. 1A is roughly half that measured with the embodiment of FIG. 1B, because the sound speed in a kidney stone (the embodiment of FIG. 1A) is roughly twice that of the sound speed in water (the embodiment of FIG. 1B).

Figure 3:
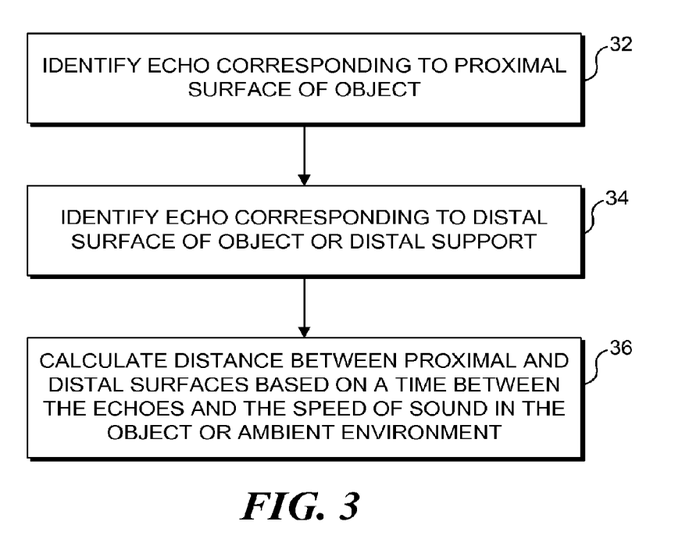
FIG. 3 is a flowchart including exemplary steps for implementing either embodiment of FIGS. 1A and 1B.

FIG. 3 is a flowchart including exemplary steps for implementing either of the embodiments of FIGS. 1A and 1B. In a step 32, an echo caused by reflection of an ultrasound pulse from a proximal surface of an object is identified in an ultrasound signal. In a step 34, an echo caused by reflection of the ultrasound pulse from either a distal surface of the object or a distal surface supporting the object (as described above) is identified in the received ultrasound signal. In a step 36, a time between the two echoes and a speed of sound in the object or in the ambient fluid are used to calculate a distance between the proximal and distal surfaces, providing an indication of a size of the object.

Figure 4A:
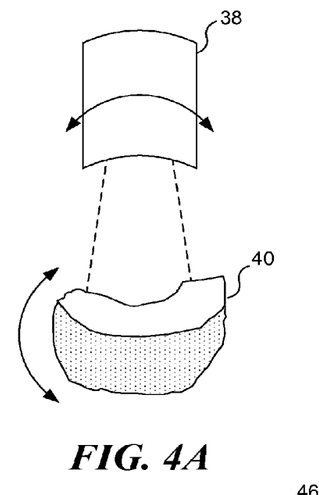
FIGS. 4A and 4B schematically illustrate an exemplary and optional additional technique for manipulating the object before implementing one of the ultrasound sizing techniques disclosed herein, to ensure that a maximum dimension of the object will be measured.
Figure 4B:
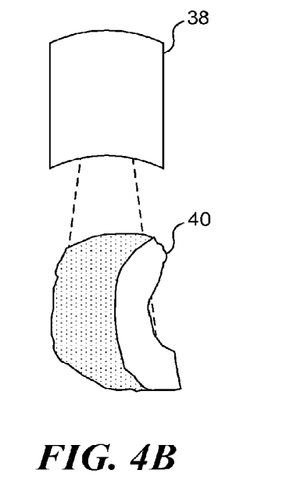

It should be recognized that the distance being measured is axial or one dimensional (i.e., a height, width, or length), while the object is three dimensional. Although in some circumstances, any dimensional information about the object will be more useful than no information, preferably, the dimension being measured should represent a maximum dimension of the object. FIGS. 4A and 4B schematically illustrate an exemplary and optional additional technique for manipulating the object before implementing one of the exemplary ultrasound sizing techniques disclosed herein, to ensure that a maximum dimension of the object is measured. An optical instrument 38 can be used to enable a user to view an object 40, and thereby determine if the object or the optical instrument needs to be repositioned so that a maximum dimension of the object is aligned with the optical instrument. Of course, the intent is to ensure that the ultrasound pulses propagate generally along the axis that is aligned with longest dimension of the object. Accordingly, after such repositioning (if required), the ultrasounds transducer is then placed in the same relative position as the optical instrument, which will achieve the alignment of the ultrasound pulse propagation path in alignment with the axis of the longest dimension of the object. In practice, the optical instrument and the ultrasound transducer can be located adjacently on a distal end of a single medical instrument (such as a ureteroscope), disposed adjacently proximate the object, or can be disposed in adjacent lumens of an elongate medical instrument, such as a catheter. Further, the optical instrument (such as a digital sensor or an optical fiber coupled to a digital sensor or an eyepiece) can be advanced through a working lumen of a medical instrument to enable the object's relative position to be visualized and corrected if needed, then removed, such that the ultrasound transducer is then advanced through the same lumen and is not oriented relative to the object to measure the maximum dimensional size of the object. Note that using a single lumen for visualization and sizing may be useful even when a relative position of the stone or instrument is not manipulated. Furthermore, when using a ureteroscope a urologist can generally discern two dimensions (i.e., height and width) to visually estimate the size. However, a third dimension, depth, is much harder to determine, and the stone may even be partially buried an unknown depth into tissue. The concepts disclosed herein can be used to measure such depth.

Figure 5A:
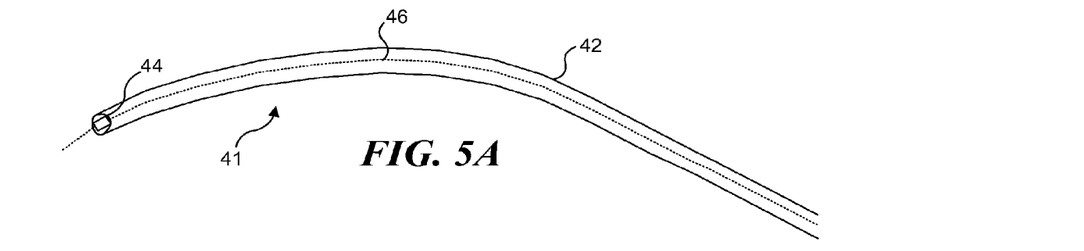
FIG. 5A schematically illustrates an exemplary medical device for implementing the ultrasound sizing techniques disclosed herein, comprising an elongate flexible body, with an ultrasound transducer disposed at a distal end of the device.

FIG. 5A schematically illustrates an exemplary medical device 41 for implementing the ultrasound sizing techniques disclosed herein. This exemplary medical device includes an elongate flexible body 42, with an ultrasound transducer 44 disposed at a distal end of the device. Depending on the location at which the medical device will be used, the medical device may (or may not—as appropriate) be designed to be used with a guidewire 46.

Figure 5B:
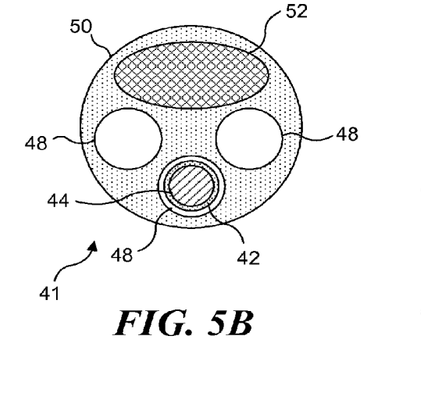
FIG. 5B schematically illustrates a first exemplary embodiment of the medical device of FIG. 5A, wherein the medical device is inserted into a working lumen of a flexible ureteroscope, to enable a size of kidney stones (and kidney stone fragments) to be measured during a ureteroscopic procedure.

FIG. 5B schematically illustrates a first exemplary embodiment of medical device 41 of FIG. 5A, wherein the medical device is inserted into a working lumen 48 of a flexible ureteroscope 50, to enable a size of kidney stones (and kidney stone fragments) to be measured during a ureteroscopic procedure. Note that as shown, flexible ureteroscope 50 includes a plurality of working lumens (though only one working lumen is required), and an optical element 52 (generally an imaging sensor, although some such instruments may employ optical fibers coupled to a remote eyepiece or image sensor). In ureteroscopes, the working lumens generally average about 3 Fr (based on the French catheter scale chart, i.e., about 1 mm). Thus, for use with ureteroscopes, medical device 41 of FIG. SA should be about 2.5 Fr (i.e., about 0.8 mm). Of course, applications of the present approach in other in vivo locations will have other sizing requirements. Providing ultrasound transducers of sufficient power, in sizes as small as 0.5 mm does not present any significant technical challenge. It should be recognized that the relative sizes, shapes, and locations of the elements shown in FIG. 5B are intended to be exemplary, and not limiting.

Figure 5C:
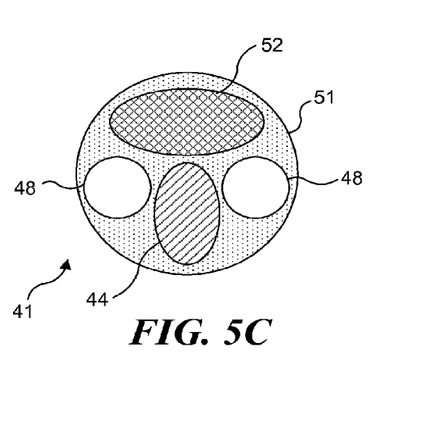
FIG. 5C schematically illustrates a second exemplary embodiment of the medical device of FIG. 5A, wherein the medical device is based on a flexible ureteroscope, modified to include an ultrasound transducer at its distal end, to enable a size of kidney stones (and kidney stone fragments) to be measured during a ureteroscopic procedure.

FIG. 5C schematically illustrates a second exemplary embodiment of medical device 41 of FIG. 5A, wherein the medical device is based on a flexible ureteroscope 51, modified to include ultrasound transducer 44 at its distal end, to enable the size of kidney stones (and kidney stone fragments) to be measured during a ureteroscopic procedure. Thus, in this embodiment, medical device 41 itself comprises flexible ureteroscope 51, which includes a plurality of working lumens (though only one working lumen is required), optical element 52 (generally an imaging sensor, although such instruments may employ optical fibers coupled to a remote eyepiece or image sensor), and ultrasound transducer 44. It should be recognized that the relative sizes, shapes, and locations of the elements shown in FIG. 5C are intended to be exemplary, and not limiting.

Figure 6A:
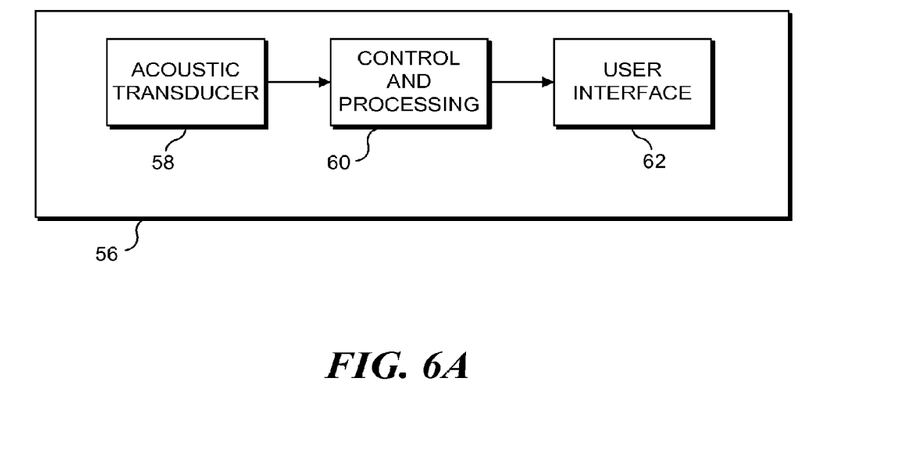
FIG. 6A schematically illustrates an exemplary system for using the medical device of FIG. 5B.

FIG. 6A schematically illustrates an exemplary system 56 for using the medical device of FIG. 5B. The system includes a medical device with an ultrasound transducer 58 at its distal end, control and processing element 60, and a user interface 62 (generally a display, although it should be recognized that other types of user interfaces, such as audible outputs, can also be beneficially employed). A personal computer or other type of computing device represents an exemplary control and processing component, although it should be recognized that other types of logical processing components can also be employed, such as custom logic circuits and application specific integrated circuits (ASICs). Processing element 60 at least enables the distance calculations discussed above to be automatically performed in response to collection of the ultrasound data (the paired echoes corresponding to reflections from the proximal and distal surfaces of the object, or from the proximal surface of the object and the backing surface that supports the distal surface of the object). In at least one exemplary embodiment, the user interface is configured to enable a user to enter a value used for the speed of sound in a particular object (or in a particular ambient fluid), or to select a value that will be used for this parameter from a plurality of options. In at least one other exemplary embodiment, processing element 60 performs the calculations using a default value for the speed of sound.

Figure 6B:
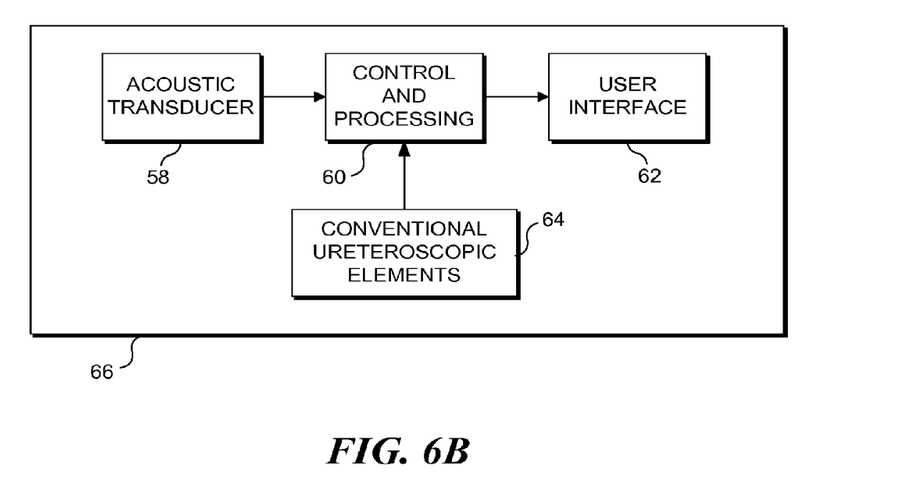
FIG. 6B schematically illustrates an exemplary system for using the medical device of FIG. 5C.

FIG. 6B schematically illustrates a similar exemplary system 66 for using the medical device of FIG. 5C. The system includes the modified ureteroscope with an ultrasound transducer 58 at its distal end, control and processing element 60, user interface 62 (generally a display, although it should be recognized that other types of user interfaces, such as audible outputs, can also be beneficially employed), and additional conventional ureteroscopic components 64. It will be appreciated that in using exemplary system 66 in connection with treating a medical condition in which a stone has formed in a patient's body, one of a number of accepted medical procedures, such as lithotripter shock waves, or laser light, will often be used to initially break the stone into a plurality of smaller fragments. The novel concept disclosed herein can then be used for measuring the size of the stone fragments to assist the medical practitioner in removing the stones through a lumen. If any stone fragment is measured and found to be too large to be removed, the procedure for fragmenting the stones may be applied again to further fragment the too large fragments, until all are of sufficiently small size to be removed through the lumen.

Figure 7A:
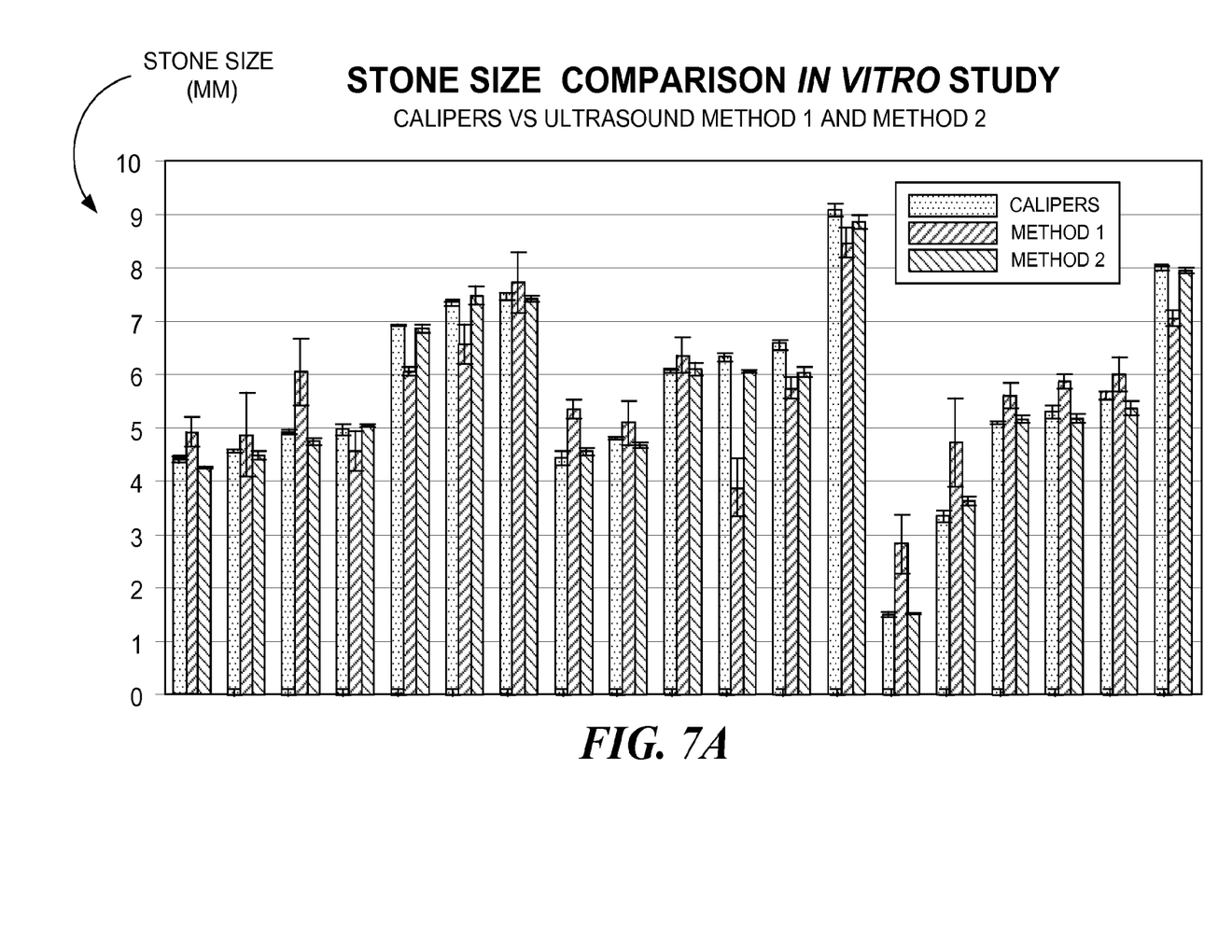
FIG. 7A graphically illustrates a first set of in vitro empirical data comparing measurements collected using calipers, the embodiment of FIG. 1A, and the embodiment of FIG. 1B.
Figure 7B:
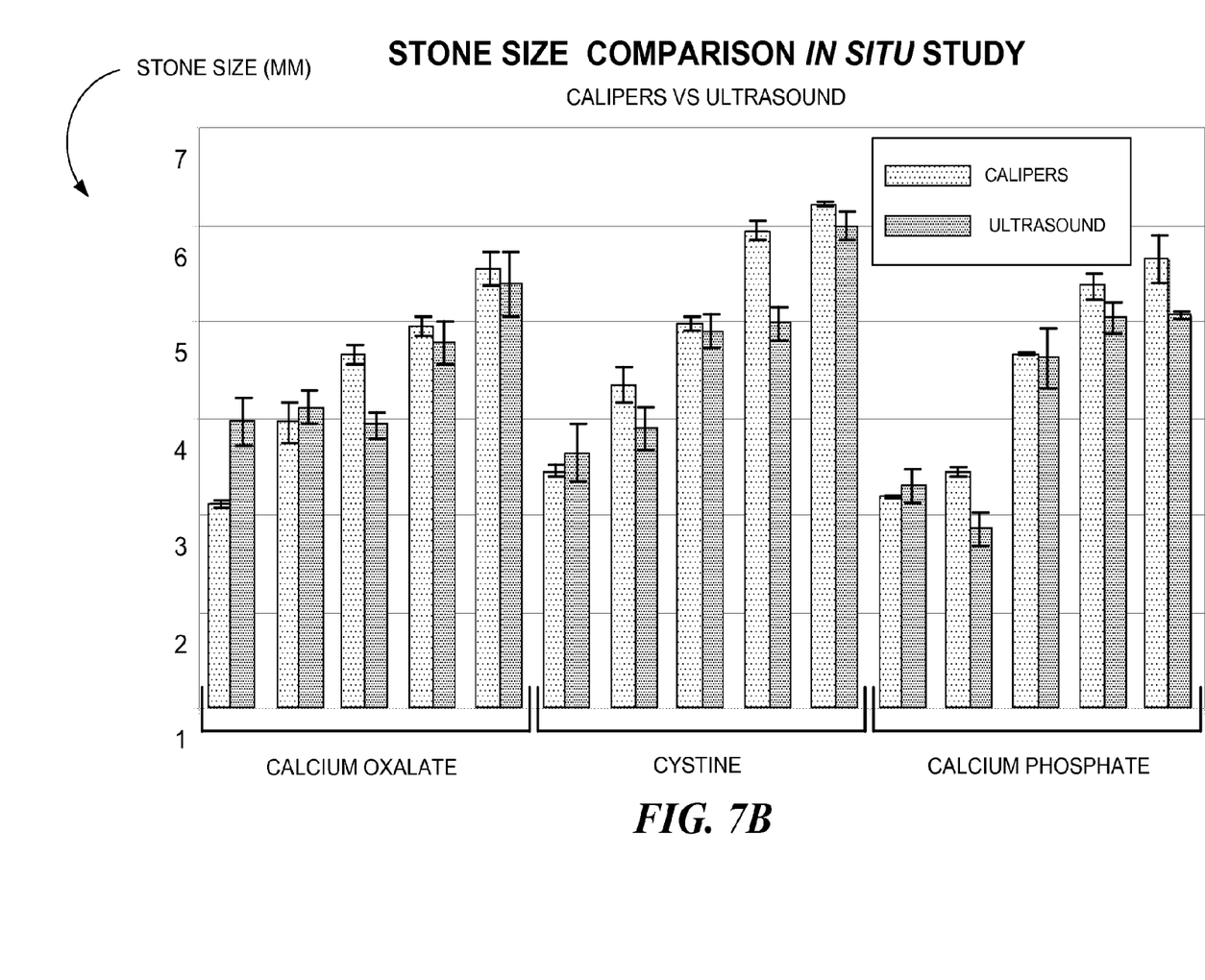
FIG. 7B graphically illustrates a second set of in situ empirical data comparing measurements collected using calipers, the embodiment of FIG. 1A, and the embodiment of FIG. 1B.

FIG. 7A graphically illustrates a first set of empirical data comparing measurements collected using calipers, the embodiment of FIG. 1A, and the embodiment of FIG. 1B, while FIG. 7B graphically illustrates a second set of empirical data comparing measurements collected using calipers, the embodiment of FIG. 1A, and the embodiment of FIG. 1B.

First Empirical Study (In Vitro)

The initial study was an in vitro study using excised kidney stones. A 10 MHz, 10 Fr transducer was used to send an ultrasound pulse toward the stone, and was also used to receive ultrasound reflections from the stone. The time between the reflections from the proximal and the distal ends of the stone was used to calculate the stone size, generally as discussed above. For this initial study, the speed of sound in the stones measured in the study was assumed to be 3000 m/s. Note that both techniques discussed above were implemented (i.e., where the second reflection was due to an echo from the distal surface of the stone, and where the second reflection was due to an echo from a distal surface supporting the distal side of the stone). The size of the stone was also measured using calipers (along the same axis measured using the ultrasound techniques).

The measurements were performed for 19 human stones, and compared by linear regression. Single stones from 19 separate patients were obtained from a stone reference laboratory. All stones were >95% pure composition. Three different types of stones (seven calcium oxalate monohydrate, six cystine, and six calcium hydrogen phosphate dihydrate), of a variety of shapes were rehydrated for 24 hours in de-ionized water. Each stone was measured three times using measurements with calipers; mean and standard deviation were recorded; and then, the stone was placed in the same orientation on a planar tissue phantom and submerged in 20° C. water.

The 10 MHz (⅛" diameter/10 Fr) transducer (Model M112™, available from Panametrics NDT (now Olympus NDT) of Waltham Mass.) transmitted and received ultrasound pulses through a pulser receiver (Model 5072PR™, Olympus NDT) at 100 Hz. The signals produced in response to the received pulses were displayed in real time on a digital oscilloscope. The operator aligned the transducer by hand and recorded three signals for each method (i.e., the respective exemplary embodiments of FIGS. 1A and 1B). The operator aligned the transducer visually, but made final position decisions by watching the oscilloscope and aligning the transducer to capture the longest time intervals. The signals were then analyzed by another investigator in a blind study to determine the time used to calculate stone size. A regression analysis between mean measurements with the calipers and ultrasound-based measurements was used to compare the data. These results are graphically presented in FIG. 7A. It should be recognized that well-known signal processing techniques can be employed to automate the process of calculating the time interval between reflections. Such signal processing can include, but is not limited to, subtraction of background interference, averaging to increase a signal to noise, de-convolution to remove an initial pulse length, and cross correlation to determine the time between the two reflections.

The embodiment of FIG. 1B (second echo reflecting from a distal surface supporting the stone) was somewhat easier to implement. Time determination for the embodiment of FIG. 1A (second echo reflecting from a distal surface of the stone itself) was more difficult to implement because of multiple scattering and reverberations within the stone. For the embodiment of FIG. 1A (second echo reflecting from a distal surface of the stone), the correlation between stone size determined with calipers and ultrasound-determined stone size was $r^2=0.71$ ($p<0.0001$), and in two stones, the deviation was greater than 1 mm. For the embodiment of FIG. 1B (second echo reflecting from a distal surface supporting the stone), the correlation was better, with $r^2=0.99$ ($p<0.0001$).

Significantly, both the embodiment of FIG. 1A and the embodiment of FIG. 1B provided useful measurements, although the results provided by the embodiment of FIG. 1B were more accurate and precise. The measurement error (i.e., precision, indicated by error bars in FIG. 7A) was less than 0.2 mm in all stones using the embodiment of FIG. 1B, and less than 1 mm in all stones using the embodiment of FIG. 1A. Accuracy was similar to the precision, except in two stones where the embodiment of FIG. 1B was in error more than 1 mm. There was no obvious consistent bias due to stone type, which could have been exhibited in measurements from the embodiment of FIG. 1A, where differences in the speed of sound in different stone types could have introduced such a bias (for example, the measurements would be lower than the true values, if the actual speed of sound in the objects were greater than 3000 m/s).

Based on the first empirical (in vitro) study, medical instrument-based ultrasound can accurately and precisely measure stone fragment size using either of the two exemplary techniques (i.e., the embodiments of FIGS. 1A and 1B). Significantly, accurate measurements were obtained when holding the transducer by hand, indicating that hand-held instruments should provide accurate measurements as well. The transducer employed (10 Fr, 30 mm) was larger than can be employed in a ureteroscope, and the signal obtained was on the magnitude of one volt. Using a smaller transducer for clinical use will reduce the signal magnitude, but it should be possible to reduce the signal well below the one volt level and still obtain data sufficient in magnitude to make an accurate measurement. This novel technique thus provides acceptable real-time fragmentation size measurements during ureteroscopy, as well as being usable for sizing other in vivo objects.

Second Empirical Study (In Situ)

The second study was carried out in situ using excised kidney stones implanted in a porcine liver. Significantly, while a smaller transducer was employed, useful measurements were still obtained, thereby confirming that the novel approach should provide the desired results when in clinical use.

In the in situ study, a 1.2 mm (3.6 Fr) ultrasound-based instrument was used to accurately and precisely measure stone fragments deep within the collecting system of a porcine kidney. In this study, 15 human stones of three types (five each of calcium oxalate, cystine, calcium phosphate), and having a variety of shapes, ranging in size from 3-7 mm, were rehydrated and placed deep in the collecting system of the lower pole of a freshly-sectioned porcine kidney. The speed of sound for the three stone types was determined using a separate reference stone. The 2 MHz, 3.6 Fr needle hydrophone was used to send and capture ultrasound pulses. The transit signal time, t, through the stone (or ambient fluid) was measured, and along with the speed of sound in the stone (or the ambient fluid), c, the thickness of each stone was calculated as explained above. Calculated stone thicknesses were compared to measurements with digital calipers. The results are graphically presented in FIG. 7B.

The speed of sound measured for the calcium oxalate stones was 4,331 m/s (±48), the speed of sound measured for the cystine stones was 4,321 m/s (±44), and the speed of sound measured for the calcium phosphate stones was 4,266 m/s (±75). A stone size was determined for all 15 stones using measurements with calipers and the embodiments of FIGS. 1A and 1B, generally as described above. Correlation between ultrasound-determined thickness and measurements with the calipers was excellent ($r2=0.90$, $p<0.0001$). Overall, ultrasound measurements underestimated stone size by 3%, but performed equally well in all three stone types. All stone measurements were accurate to within 1 mm, and 10 (66%) stone measurements were accurate within 0.5 mm.

It should be noted that in the first empirical study (i.e., the ex vivo study), it was assumed that the speed of sound in the human kidney stones was 3000 m/s, and rather than processing the signal to specifically identify the beginning of the first and second echoes, the total duration of the first and second echoes was employed. In the second empirical study (i.e., the in situ study), the speed of sound in the different stone types was actually measured before the stones were implanted in the porcine kidney, and signal processing techniques were employed to specifically identify the beginning of the first and second echoes. While the techniques employed in the second empirical study (i.e., the in situ study) provided more accurate results, it is significant to note that the approximations employed in the first empirical study (i.e., the ex vivo study) introduced only a minor amount of error, such that useful results were provided using the techniques in the first empirical study (i.e., the ex vivo study). In the second empirical study (i.e., the in situ study), the beginning of the first and second echoes were determined by de-convolving the basic shape of the pulse from the echo signal detected (the artisan of ordinary skill will be familiar with such processing).

All calculations of signal transit time used to determine stone thickness were performed using signals processed to remove background noise and interference (caused by the initial excitation of the transducer to produce the pulse before the transducer is used to receive the pulse). Note that additional signal processing may further improve accuracy and facilitate automation of measurements. As noted above, additional signal processing can include averaging to increase a signal to noise, de-convolution to remove an initial pulse length, and cross correlation to determine the time between the two reflections.

Significantly, in both the in vitro and in situ studies, the ultrasound signals were captured in real time, and processed offline. Real time processing is certainly achievable, since the calculations do not require significant computational resources. Once the calculations are performed, the result can be visually displayed to a user, or audibly output to a user, in real time.

While smaller instruments are generally preferable, and as a result, a single transducer will be employed in many embodiments, it should be recognized that a first acoustic emitter and a second acoustic receiver could also be employed. Measurements might also be done from orthogonal directions to better estimate a maximum dimension without reorienting/repositioning the object or a single ultrasound transducer.

While the concepts disclosed herein should be particularly well suited for use in the removal and treatment of in vivo mineral stones, it should be recognized that such concepts can also be beneficially applied in measuring the size of discrete masses of soft tissue (or of a foreign object present in the body). The medical fees for many procedures, such as treatment of a tumor, are based on a size of the tissue mass, thus the techniques disclosed herein will enable tumor size to be easily and accurately determined during a medical procedure, for determining billings.

With respect to the claims that follow, the term "approximately" should be considered to encompass a stated value, plus or minus 10%.

As discussed above, while the use of ultrasound (i.e., sound above the range of human hearing, generally accepted to be sound having a frequency of greater than about 20,000 Hz) represents an exemplary implementation, it should be recognized that similar results could possibly be obtained using different frequencies not normally associated with the term ultrasound. Thus, in the claims that follow, the more general terms acoustic transducer, acoustic energy and acoustic pulse have been employed.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

What is claimed is:
1. A method for calculating a size of an in vivo object, wherein the in vivo object comprises a proximal surface and a distal surface, the method comprising:
visualizing the in vivo object using an optical instrument in order to determine whether the in vivo object is resting on a tissue surface and surrounded by a fluid or whether the in vivo object is surrounded by tissue;
aligning an acoustic transducer of a device with the in vivo object based on the determination;
energizing the aligned acoustic transducer of the device to generate an interrogation pulse such that the interrogation pulse from the acoustic transducer travels to a proximal surface of the in vivo object;
collecting a first reflected acoustic signal portion generated in response to the interrogation pulse being reflected from the proximal surface of the in vivo object;
collecting a second reflected acoustic signal portion generated in response to the interrogation pulse being reflected from the distal surface of the in vivo object;
quantitatively calculating the size of the in vivo object as a function of: (1) a time interval between the portion of the interrogation pulse reflected from the proximal surface of the in vivo object and the portion of the interrogation pulse reflected from the distal surface of the in vivo object, and (2) an approximate speed of sound in the in vivo object, wherein the approximate speed in the in vivo object is different than a speed in a material surrounding the in vivo object.

2. The method of claim 1, wherein the method further comprises:
graphically displaying the reflected acoustic signal;
visually identifying a first peak in the empirical data corresponding to the portion of the interrogation pulse reflected from the proximal surface of the in vivo object
visually identifying a second peak in the empirical data corresponding to the portion of the interrogation pulse reflected from the distal surface of the in vivo object; and
identifying a timing of the first peak and a timing of the second peak.

3. The method of claim 1, wherein the portion of the interrogation pulse reflected from the proximal surface of the in vivo object corresponds to a first peak in the empirical data; and wherein the portion of the interrogation pulse reflected from the distal surface of the in vivo object corresponds to a second peak in the empirical data; and wherein the method further comprises:
identifying the first peak and the second peak automatically using a signal processor.

4. The method of claim 3, wherein the signal processor identifies the first peak and the second peak by at least:
removing interference caused by an initial excitation of the acoustic transducer to produce the interrogation pulse before collecting the reflected acoustic signal; or
averaging a plurality of collected reflected acoustic signal.

5. The method of claim 1, further comprising:
when the in vivo object is resting on a tissue surface and surrounded by a fluid, offsetting the acoustic transducer relative to the in vivo object such that a portion of the interrogation pulse from the acoustic transducer passes through the fluid alongside the in vivo object and encounters the tissue surface supporting the in vivo object; and
quantitatively calculating the size of the in vivo object as a function of: (1) a time interval between the portion of the interrogation pulse reflected from the proximal surface of the in vivo object and the portion of the interrogation pulse reflected from a tissue surface supporting the distal surface of the in vivo object and (2) an approximate speed of sound in the fluid surrounding the in vivo object.

6. The method of claim 1, wherein the interrogation pulse comprises approximately 5 cycles of a frequency of the acoustic transducer.

7. The method of claim 1, wherein the step of aligning comprises aligning the ultrasound transducer along a maximum dimension of the in vivo object.

8. The method of claim 1, wherein the step of aligning comprises manipulating an orientation of the in vivo object relative to the acoustic transducer such that the interrogation pulse propagates and reflects along a maximum dimension of the in vivo object.

9. A system for use by an operator for calculating a size of an in vivo object, the in vivo object comprises a proximal surface and a distal surface, the system comprising:
a device comprising an elongate body with a distal end configured to be inserted within a patient and positioned proximate to the in vivo object, the distal end of the device including one or more acoustic transducers for emitting an interrogation pulse, and wherein the one or more acoustic transducers are configured for collecting a reflected acoustic signal;
a controller in communication with the device and configured to:
receive operator input for energizing the acoustic transducer of the in vivo device to generate the interrogation pulse;
collect a first reflected acoustic signal portion generated in response to the interrogation pulse, the first reflected acoustic signal portion comprising a portion of the interrogation pulse reflected from the proximal surface of the in vivo object; and
collect a second reflected acoustic signal portion generated in response to the interrogation pulse, the second reflected acoustic signal portion comprising a portion of the interrogation pulse reflected from the distal surface of the in vivo object;
quantitatively calculate the size of the in vivo object as a function of: (1) a time interval between the portion of the interrogation pulse reflected from the proximal surface of the in vivo object and the portion of the interrogation pulse reflected from the distal surface of the in vivo object, and (2) an approximate speed of sound in the in vivo object, wherein the approximate speed in the in vivo object is different than a speed in a material surrounding the in vivo object.

10. The system of claim 9,
wherein the system further comprises one or more displays in communication with the controller; and
wherein the controller is further configured to:
output the reflected acoustic signal to the one or more displays; and
receive operator input defining a first peak in the empirical data corresponding to the portion of the interrogation pulse reflected from the proximal surface of the in vivo object; and
receive operator input defining a second peak in the empirical data corresponding to the portion of the interrogation pulse reflected from the distal surface of the in vivo object corresponds to a second peak in the empirical data.

11. The system of claim 9, wherein the portion of the interrogation pulse reflected from the proximal surface of the in vivo object corresponds to a first peak in the empirical data; and wherein the portion of the interrogation pulse reflected from the distal surface of the in vivo object corresponds to a second peak in the empirical data; and
wherein the controller automatically identifies the first and second peak from the reflected acoustic signal using signal processing.

12. The system of claim 10, wherein the controller identifies the first peak and the second peak from the reflected acoustic signal by at least:
removing interference caused by an initial excitation of the acoustic transducer to produce the interrogation pulse before collecting the reflected acoustic signal; or
averaging a plurality of collected reflected acoustic signals.

13. The system of claim 10, wherein the controller identifies the first peak and the second peak from the reflected acoustic signal by deconvolution.

14. The system of claim 9, wherein the interrogation pulse comprises approximately 5 cycles of a frequency of the acoustic transducer.

15. The system of claim 9, wherein the distal end of the device includes two acoustic transducers for emitting interrogation pulses at different angles toward the in vivo object such that multiple measurements of the in vivo object may be obtained without reorienting or repositioning the in vivo object relative to the acoustic transducers.

16. The system of claim 14, wherein the two acoustic transducers are oriented to take orthogonal measurements of the in vivo object.

17. The system of claim 9, further comprising a user interface configured to receive operator input identifying a speed of sound for quantitatively calculating the size of the in vivo object.

18. The system of claim 15, wherein the user interface is configured to display a plurality of speed of sound options for user selection, the plurality of speed of sound options including a speed of sound in a fluid, a speed of sound in a tissue mass, and a speed of sound in a stone.

19. The system of claim 9, further comprising an optical instrument in communication with a display, the optical instrument configured to provide a view of the in vivo object relative to the acoustic transducer to the operator, thereby allowing the operator to align the acoustic transducer with the in vivo object.

20. A method for calculating a size of an in vivo object, wherein the in vivo object comprises a proximal surface and a distal surface, the method comprising:

aligning an acoustic transducer of a device with the in vivo object such that an interrogation pulse from the acoustic transducer travels at least to a proximal surface of the in vivo object;

energizing the acoustic transducer of the in vivo device to generate the interrogation pulse;

collecting a first reflected acoustic signal portion generated in response to the interrogation pulse, the first reflected acoustic signal portion comprising empirical data including a portion of the interrogation pulse reflected from the proximal surface of the in vivo object;

collecting a second reflected acoustic signal portion generated in response to the interrogation pulse, the second reflected acoustic signal portion comprising either: (1) a portion of the interrogation pulse reflected from the distal surface of the in vivo object or (2) a portion of the interrogation pulse reflected from a tissue surface supporting the distal surface of the in vivo object;

quantitatively calculating the size of the in vivo object as a function of: a total time duration starting from a start of the first reflected acoustic signal portion and ending with an end of the second reflected acoustic signal portion.

\* \* \* \* \*